United States Patent
Palanker

(10) Patent No.: US 9,498,295 B2
(45) Date of Patent: Nov. 22, 2016

(54) OPTIMIZATION OF LASER THERAPY

(75) Inventor: Daniel V. Palanker, Sunnyvale, CA (US)

(73) Assignee: TOPCON MEDICAL LASER SYSTEMS, INC., Santa Clara, CA (US)

( * ) Notice: Subject to any disclaimer, the term of this patent is extended or adjusted under 35 U.S.C. 154(b) by 289 days.

(21) Appl. No.: 13/565,745

(22) Filed: Aug. 2, 2012

(65) Prior Publication Data

US 2013/0204235 A1    Aug. 8, 2013

Related U.S. Application Data

(60) Provisional application No. 61/514,419, filed on Aug. 2, 2011.

(51) Int. Cl.
*A61B 19/00*  (2006.01)
*A61F 9/008*  (2006.01)

(52) U.S. Cl.
CPC ............. *A61B 19/50* (2013.01); *A61B 34/10* (2016.02); *A61F 9/008* (2013.01); *A61F 9/00823* (2013.01); *A61F 2009/00878* (2013.01)

(58) Field of Classification Search
CPC ............ A61F 2009/00897; A61F 9/008; A61F 9/00823; A61F 2009/00878; A61B 2018/00636; A61B 19/50; A61B 34/10
See application file for complete search history.

(56) References Cited

U.S. PATENT DOCUMENTS

| 7,766,903 | B2 | 8/2010 | Blumenkranz et al. |
| 2006/0161145 | A1 | 7/2006 | Lin et al. |
| 2008/0188838 | A1 | 8/2008 | Abe |
| 2011/0166558 | A1 | 7/2011 | Dai et al. |
| 2012/0239015 | A1* | 9/2012 | Liesfeld et al. ............. 606/4 |

FOREIGN PATENT DOCUMENTS

| JP | 2009-513279 A | 4/2009 |
| JP | 2010-508120 A | 3/2010 |
| WO | 2008/060500 A2 | 5/2008 |

OTHER PUBLICATIONS

Jain et al., "Effect of Pulse Duration on Size and Character of the Lesion in Retinal Photocoagulation", Archives of Ophthalmology, vol. 126, No. 1, Jan. 2008, pp. 78-85.
International Search Report and Written Opinion received for PCT Patent Application No. PCT/US2012/049402, mailed on Oct. 16, 2012, 12 pages.

(Continued)

*Primary Examiner* — Gary Jackson
*Assistant Examiner* — Scott T Luan
(74) *Attorney, Agent, or Firm* — Morrison & Foerster LLP

(57) ABSTRACT

Systems and processes for the optimization of laser treatment of an eye are disclosed. The process can include receiving a set of parameters of a laser treatment (e.g., an aerial beam size, contact lens, pulse duration, and the desired clinical grade), determining an estimated size of a lesion to be generated by the laser treatment beam, receiving a lesion pattern density (e.g., full grid, mild grid, or other), and determining a recommended pattern of laser treatment beam spots. The recommended pattern of laser treatment beam spots may include a recommended number of laser treatment spots and a spacing between the spots.

35 Claims, 5 Drawing Sheets

(56) References Cited

OTHER PUBLICATIONS

International Preliminary Report on Patentability received for PCT Patent Application No. PCT/US2012/049402, mailed on Feb. 13, 2014, 11 pages.
Extended European Search Report (includes Supplementary European Search Report and Search Opinion) received for European Patent Application No. 12820210.8, mailed on Feb. 18, 2015, 5 pages.
Barrett et al., "Digital Tracking and Control of Retinal Images", Optical Engineering, vol. 33, No. 1, Jan. 1994, pp. 150-159.
Office Action received for Japanese Patent Application No. 2014-524091, mailed on Jul. 4, 2016 (6 pp. with English translation).

* cited by examiner

OPTIMIZATION OF LASER THERAPY

CROSS-REFERENCE TO RELATED APPLICATION

This application claims the benefit, under 35 U.S.C. §119(e), of U.S. Provisional Patent Application No. 61/514,419, filed Aug. 2, 2011, and entitled "LESION PATTERNS FOR RETINAL PHOTOCOAGULATION," the contents of which are incorporated by reference in its entirety for all purposes.

BACKGROUND

1. Field

This relates generally to ocular laser treatments and, more specifically, to optimization of photothermal therapy of the eye.

2. Related Art

Every year, thousands of patients in the United States and other countries undergo laser-based interventional treatments of the eye. Such treatments typically involve the application of laser energy in the form of a laser treatment beam having a controlled power and controlled duration to targeted tissue structures to create visible or sub-visible lesions. These treatments may be used to address clinical problems, such as diabetic retinopathy, diabetic macular edema, neovascular disease, age-related macular degeneration, glaucoma, retinal vascular leakage resulting from angiogenic factors produced in response to retinal inflammation and ischemia, or the like.

One conventional laser-based treatment that may be used to treat the eye is retinal photocoagulation, which may typically be performed with a 514 or 532 nm laser using exposure durations from 50 to 200 ms and spot sizes ranging from 100 to 500 µm. Early retinal photocoagulation techniques included the application of relatively intense retinal lesions, resulting in thermal damage that undesirably extended into the inner retina. More recent retinal photocoagulation techniques include the application of moderate lesions to limit damage to the ganglion cell layer and nerve fiber layer of the eye. Even more recently, a retinal photocoagulation technique has been developed that includes the application of patterns of multiple spots onto the eye using a scanning laser. These applications of patterned spots can be applied with shorter pulse durations in the range of 10-30 ms. Since heat diffusion is decreased due to shorter exposure time, these lesions tend to be lighter and smaller than their single-point counterparts.

Using any one of the laser treatment techniques described above, physicians may treat a patient's eye using multiple laser treatment beam applications to form multiple lesions over a desired portion of the eye. For example, physicians currently apply a single application of the laser treatment beam to patient's eye and observe the resulting lesion. The physician may then apply another application of the laser treatment beam at a location near the previously generated lesion. Typically, the location of the subsequent laser treatment beam application is determined by the physician and the distance between successive laser treatment beam applications corresponds to a certain fraction of the lesion diameter. In this way, the physician may generate a pattern of multiple lesions over a desired treatment area of the patient's eye.

While this technique may be used to effectively treat a patient using a single-spot laser treatment beam that generates visible lesions, it may not be used to treat a patient using a laser treatment beam that generates sub-visible lesions, as the physician would be unable to position the laser treatment beam based on a previously formed sub-visible lesion. Moreover, this technique may not be used to treat a patient using a patterned laser treatment beam since the pattern should be determined prior to the application of the patterned laser treatment beam.

SUMMARY

Systems and processes for the optimization of laser treatment of an eye are provided. The process can include receiving a set of parameters of a laser treatment beam (e.g., an aerial beam size, contact lens, pulse duration, and the desired clinical grade), determining an estimated size of a lesion to be generated by the laser treatment beam, receiving a desired lesion pattern density (e.g., full grid, mild grid, or other), and determining a recommended pattern of laser treatment beam spots. The recommended pattern of laser treatment beam spots may include a recommended number of laser treatment spots, its density, and spacing between the spots.

The process may further include obtaining reference data comprising pairs of sets of laser treatment parameters and estimated lesion sizes. In some examples, the reference data may be obtained by measuring a width of the coagulated zone in the eye for a broad range of laser parameters, such as different beam sizes on the eye, pulse durations, and clinical grades, representing a range of applicable laser settings in photocoagulation. The measurement and associated data can be stored in a reference database.

The process may further include querying the reference database using the set of parameters of the laser treatment beam. Based on the querying of the reference database, the recommended pattern of laser treatment beam spots may be determined. If the received parameters do not match directly with those stored in the reference database, the process may include interpolating the estimated size of the lesion based on the measured values stored in the database.

DETAILED DESCRIPTION

In the following description of the disclosure and examples, reference is made to the accompanying drawings in which it is shown by way of illustration specific examples that can be practiced. It is to be understood that other examples can be practiced and structural changes can be made without departing from the scope of the disclosure.

As described above, laser-treatment systems are commonly used to deliver laser energy to targeted portions of the eye in order to create lesions or increase the temperature of the eye at desired locations. The systems and processes described herein may be used to provide a user with a recommended pattern of laser treatment beam spots (e.g., including a number and spacing of laser treatment beam applications) that may be applied to a patient's eye based on user-provided parameters.

Figure 1:
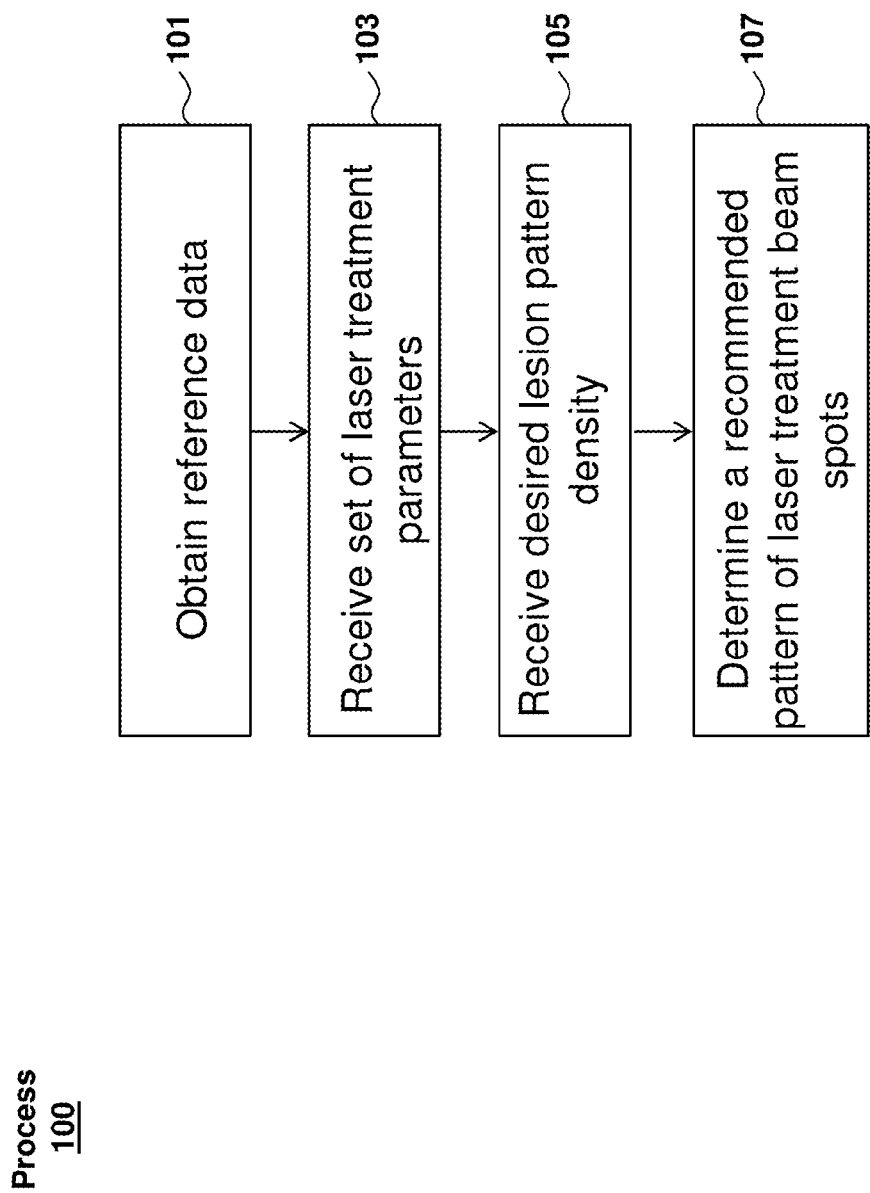
FIG. 1 illustrates an exemplary process for determining a recommended pattern of laser treatment beam spots.
Figure 2:
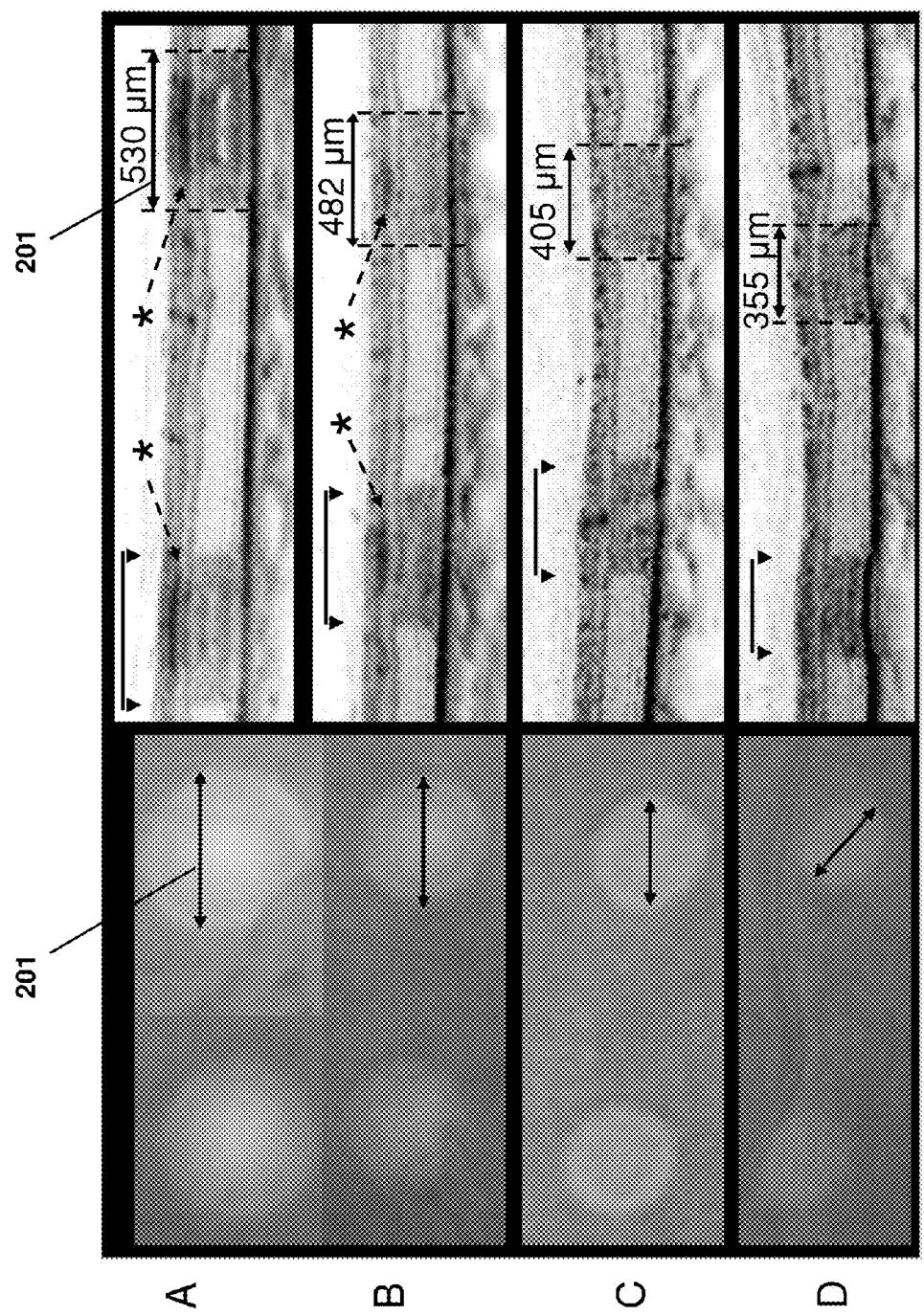
FIG. 2 illustrates views of exemplary acute lesions formed by laser treatment beams having varying laser treatment parameters.

FIG. 1 illustrates an exemplary process 100 that can be performed by a laser-treatment system to determine a recommended pattern of laser treatment beam spots based on a set of laser treatment parameters. At block 101, reference data may be obtained. The reference data may include one or more sets of laser treatment parameters and associated lesion sizes. In one example, the reference data may be obtained by applying laser treatment beams having varying parameters to an eye and observing the resulting visible lesion, sub-visible lesion, or temperature change caused by the various laser treatment beams. For example, using optical coherence tomography (OCT), fundus photography, or the like, the sizes of the coagulation zone generated using various laser settings can be measured. FIG. 2 shows example OCT and fundoscopic views of acute lesions (generated using 400 μm aerial beam size) having coagulated zone widths 201 caused by a laser treatment beam application having a (A) 100 ms laser exposure duration, resulting in a moderate grade lesion; (B) 20 ms laser exposure duration, resulting in a moderate grade lesion; (C) 20 ms laser exposure duration, resulting in a light grade lesion; and (D) 20 ms laser exposure duration, resulting in a barely visible grade lesion.

The laser treatment parameters and data associated with the resulting lesions may be stored in a multidimensional reference database. The reference database may later be used to predict lesion size for various laser settings based on either direct reference to the database or interpolation. Table 1, shown below, illustrates example reference data that may be stored in the reference database. Table 1 shows the relationship between aerial beam size, pulse duration, and desired clinical grade of the lesion. While specific values are provided, it should be appreciated that other values may be used based on the data obtained at block 101

TABLE 1

| Relationship between the lesion width, the aerial beam size, pulse durations, and clinical grades. | | | | | | | |
|---|---|---|---|---|---|---|---|
| beam in | beam on | moderate | | light | | barely visible | |
| air | retina | 100 ms | 20 ms | 100 ms | 20 ms | 100 ms | 20 ms |
| 100 μm | 94 μm | 3.81 ± 0.98 | 2.50 ± 0.30 | | 2.08 ± 0.24 | | |
| 200 μm | 188 μm | 2.08 ± 0.22 | 1.49 ± 0.09 | | 1.24 ± 0.08 | | 0.93 ± 0.08 |
| 400 μm | 376 μm | 1.39 ± 0.08 | 1.15 ± 0.07 | 1.19 ± 0.11 | 0.99 ± 0.09 | 0.99 ± 0.08 | 0.74 ± 0.12 |

It should be appreciated that the reference database may store the reference data in different ways. In one example, the reference database may include each pair of sets of laser treatment parameters and resulting lesion size. In another example, average lesion sizes may be stored in associated with a set of laser treatment parameters. In yet another example, a mathematical model may be generated based on the reference data stored in the reference database.

At block 103, a set of laser treatment parameters may be received. In some examples, the set of parameters may include one or more of aerial beam size, contact lens specifications (e.g., type of contact lens, magnification factor of the contact lens, or the like), pulse duration, and clinical grade of the desired lesion. For example, the system may receive a set of laser treatment parameters (e.g., the aerial beam size, contact lens specifications, pulse duration, and clinical grade of the desired lesion) from a physician or other user of the system.

At block 105, a lesion pattern treatment density (or desired spacing between the lesions) may be received. For example, the system may receive the desired lesion pattern treatment density from the physician or other user.

At block 107, the system may determine a recommended pattern of laser treatment beam spots, where the laser treatment beam spots are arranged to generate the lesion pattern density received at block 105. In some examples, determining a recommended pattern of laser treatment beam spots may include determining a number of laser treatment beam spots to be applied and a spacing between the laser treatment beam spots. In some examples, to determine the number of laser treatment beam spots and the spacing between the laser treatment beam spots, the system may determine an expected lesion size based on the set of laser treatment parameters received at block 103 (e.g., aerial beam size, contact lens specifications, pulse duration, and clinical grade of the desired lesion) and the reference data stored in the reference database. For example, the system can identify a data point that includes the exact parameter values as those received at block 103 (e.g., reference data entry having the same set of laser treatment parameters) and output the corresponding lesion size. If, however, there is no exact match between the parameter values received at block 103 and the reference data stored in the reference database, the system may interpolate the estimated lesion size based on the reference data. For example, a mathematical model may be generated based on the reference data and may be used to perform a linear or non-linear interpolation.

The system may then determine a recommended number of laser treatment beam spots to be delivered and spacing between the spots in the treatment pattern in order to coagulate a certain area of the retina (or other portion of the eye). A more detailed description of the determination performed at block 107 is described below with reference to FIG. 3.

While process 100 includes blocks shown in a particular order, it should be appreciated that the blocks may be performed in any order. Moreover, process 100 may include all or a subset of blocks shown in FIG. 1. For example, block 101 may not be performed if the reference database has already been generated. Instead, the existing reference database can be used to perform blocks 103, 105, and 107.

Figure 3:
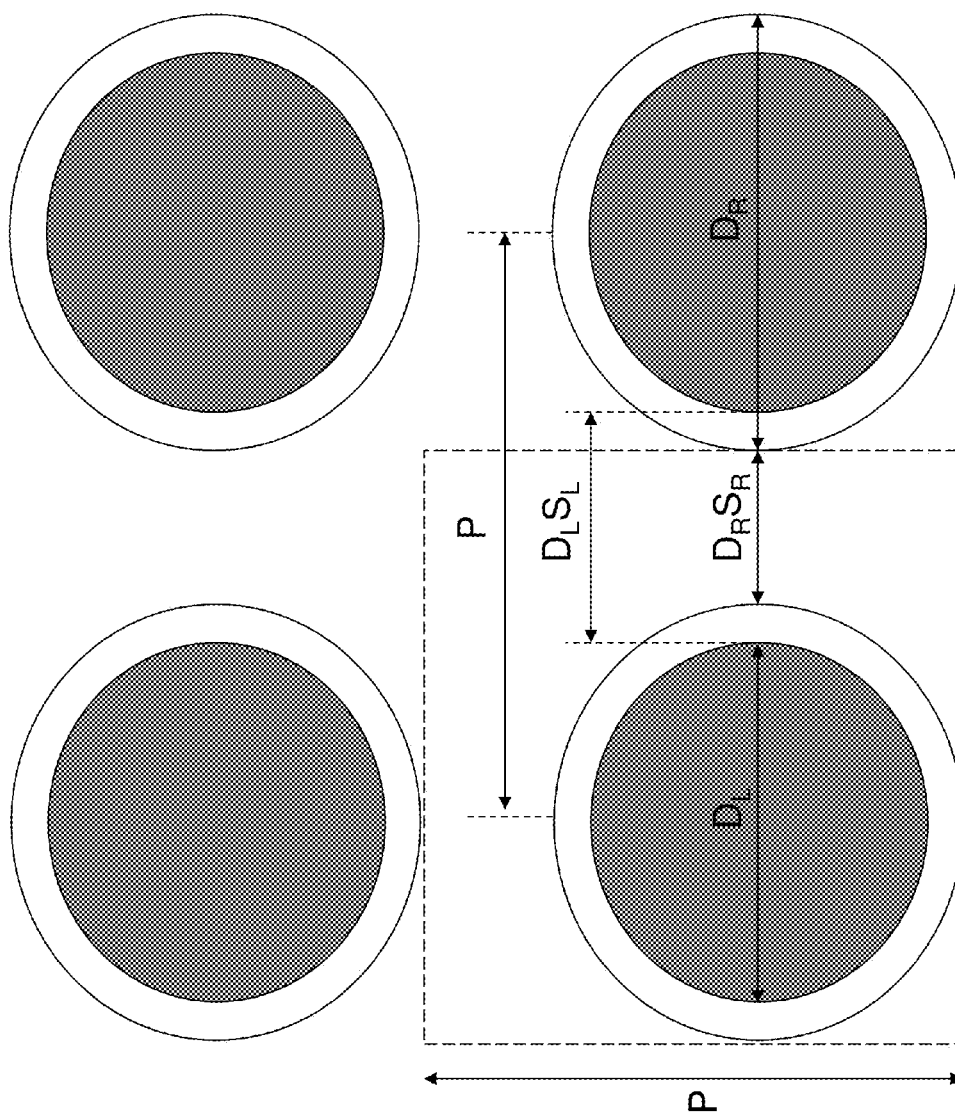
FIG. 3 illustrates an exemplary pattern of laser treatment beam spots that may be generated using the process of FIG. 1.

FIG. 3 illustrates an exemplary pattern of four laser spots that may be generated or recommended using process 100, where P is the period of the laser pattern, $D_L$ is the diameter of the laser spot on the retina, $D_R$ is the diameter of the lesion, $S_L$ is the relative spacing between laser spots (edge-to-edge, in units of beam diameter), and $S_R$ is the resulting relative spacing between the lesions (in units of lesion diameter).

In some examples, full scatter pan retinal photocoagulation (PRP) treatment may include spacing the lesions by half of the lesion diameter $D_R$ and mild scatter PRP treatment may include spacing the lesions by one lesion diameter $D_R$. The fraction of the coagulated area in the retina is determined by the ratio of the area of a lesion ($\pi D_R^2/4$) to the area of one period in the pattern ($P^2$): $F=\pi D_R^2/4P^2$. Since $P=D_R(1+S_R)$, $F=\pi/4(1+S_R)^2$. For example, mild scatter ($S_R=1$) involves coagulation of approximately 20% of the retina, while full scatter ($S_R=0.5$) involves coagulation of up to 34% of the retina in the treatment zone.

To determine a semi-automated pattern application, the spacing between the laser spots ($S_L$) may be related to the resulting spacing between the lesions ($S_R$). The pattern period can be expressed as a function of both parameters: $P=D_R(1+S_R)=D_L(1+S_L)$. Relating the resulting lesion size to a beam diameter: $D_R=D_L \cdot g$, (coefficient g is a function of the lesion grade, pulse duration and aerial beam size, shown for some parameters in Table 1), allows expressing the spacing between the laser spots as the following: $S_L=g(1+S_R)-1$. For example, for light grade lesions generated using a 20 ms pulse duration of a laser treatment beam having a 400 μm aerial beam width, g may have a value close to 1. Thus, the beam spacing may be equal or almost equal to the resulting lesion spacing. In another example using barely visible lesions (g=0.74), the spacing of lesions may be much tighter. If a comparable area is to be coagulated: $S_L=0.11$ instead of 0.5 diameter for a full scatter, and $S_L=0.48$ instead of 1 for a mild scatter may be used.

If a contact lens is used, the beam size may be scaled reciprocal to the lens magnification factor. For example, if the lens magnifies the image by a factor of two, then the beam size on the retina is de-magnified by the same amount. Table 2, shown below, lists example image magnification factors and their reciprocals (e.g., the beam magnification factor (L)) for some common contact lenses. Taking into account magnification of the beam size by a beam magnification factor L (see Table 2) $D_L=L \cdot D$, where D is a laser beam diameter in the air: $P=L \cdot D \cdot (1+S_L)$ the total number of required lesions can be calculated by dividing the total area of the target treatment area $S_{ret}$ by the area of a unit period ($P^2$): $N=S_{ret}/P^2=S_{ret}/(L \cdot D \cdot (1+S_L))^2$. With an average eye diameter of 22 mm, the area posterior to the equator $S_{ret}=760$ mm² (the total retinal area is about 1050 mm², but its portion anterior to the equator is easily accessible only with an endoscope, or scleral depression). However, other values of $S_{ret}$ can be used and can correspond to any desired target treatment area of the eye. Thus the total number of lesions N can be calculated as a function of beam diameter in air D (in mm), lens magnification factor L, lesion grade factor g, and desired lesion spacing factor $S_R$ as following: $N=760/(L \cdot D \cdot g \cdot (1+S_R))^2$.

TABLE 2

List of ocular contact lenses and their magnifications in a human eye.

| Lens | Image Magnification | Laser beam magnification |
|---|---|---|
| Ocular Mainster Std | 0.95 | 1.05 |
| Ocular Fundus Laser | 0.93 | 1.08 |
| Ocular Karichoff Laser | 0.93 | 1.08 |
| Ocular 3 Mirror Univ. | 0.93 | 1.08 |
| Ocular Mainster Wide | 0.67 | 1.50 |
| Ocular Mainster Ultra | 0.53 | 1.90 |
| Ocular Mainster 165 | 0.51 | 1.96 |
| Rodenstock Panfundoscope | 0.67 | 1.50 |
| Volk G-3 Gonio | 1.06 | 0.94 |
| Volk Area Centralis | 1.06 | 0.94 |
| Volk TransEquator | 0.69 | 1.44 |
| Volk SuperQuad 160 | 0.5 | 2.00 |
| Volk QuadrAspheric | 0.51 | 1.97 |
| Volk HRWF | 0.5 | 2.00 |
| Goldmann 3 mirror | 1.00 | 1.00 |

For example, with a beam in air of D=200 μm (0.2 mm), and a lens magnification L=2 (Volk SuperQuad 160) the beam size will be $D_L=400$ μm. Since for 20 ms light lesions g≈1, they will have the same diameter $D_R=g \cdot D_L=400$ μm. Full scatter ($S_R=0.5$) will have a period $P=D_R(1+S_R)=600$ μm, and thus the number of lesions $N=S_{ret}/P^2=760/0.36=2111$. With barely visible lesions (g=0.74) the total number for a full scatter would be N=3855. With the same beam diameter, the corresponding number of 20 ms moderate lesions (g=1.15) for a full scatter is N=1596. With the 100 ms moderate lesions (g=1.39) the same area is covered by 1093 spots.

In some examples, the size of the target treatment area of the eye can be received from a user prior to block 107 being performed. For example, a physician may input a desired treatment area and the system, using the processes and equations described above, may return a pattern of laser treatment beam spots specifying a number of laser treatment spots and a spacing between the spots that will form lesions within the desired treatment area and having the desired lesion pattern density. In this way, the physician need only provide the set of laser treatment parameters, a desired treatment area, and a desired lesion pattern density. Based on this information, the system may recommend a pattern of laser treatment beam spots for the physician to apply to the target treatment area.

Using process 100 to determine a recommended pattern of laser treatment beam spots prior to the application of the laser treatment beam allows a user to properly apply multiple laser treatment beam applications to form lesions over a desired treatment area. This provides an improvement over conventional single spot (non-patterned) photocoagulation where the physician or other user typically observes the lesion from the previous exposure and places next pulse at the distance corresponding to a certain fraction of the lesion diameter. In particular, if forming sub-visible lesions, the physician or other user would be unable to position the next pulse based on a previously formed sub-visible lesion. Using process 100, however, would allow a user to form a desired pattern of lesions since it does not rely on positioning a subsequent pulse based on previously formed visible lesion. Thus, in some examples, the reference database may include data associated with sub-visible lesions observed using image modalities, such as OCT. This may result in appropriate spacing of sub-visible lesions that would not be possible using conventional techniques.

Moreover, using conventional photocoagulation techniques, patterned laser treatment beam delivery is not possible since the entire pattern must be determined prior to the application of the patterned laser. Thus, process 100 advantageously allows a user to set the spot spacing properly ahead of time, since lesions can be larger or smaller than the laser spots, depending on the settings.

In some examples, the reference database may further be updated and adjusted to reflect personal preferences of the physician or user. For example, there is subjectivity to the process of defining the clinical grade of a lesion (intense, light, barely visible, etc.), and physicians may have slightly varying scales. The system user can measure the lesions (ophthalmoscopcially, or with OCT or other imaging modality) that are produced under various clinical grades and store the values in the database, thereby personalizing it to his/her practice.

Figure 4:
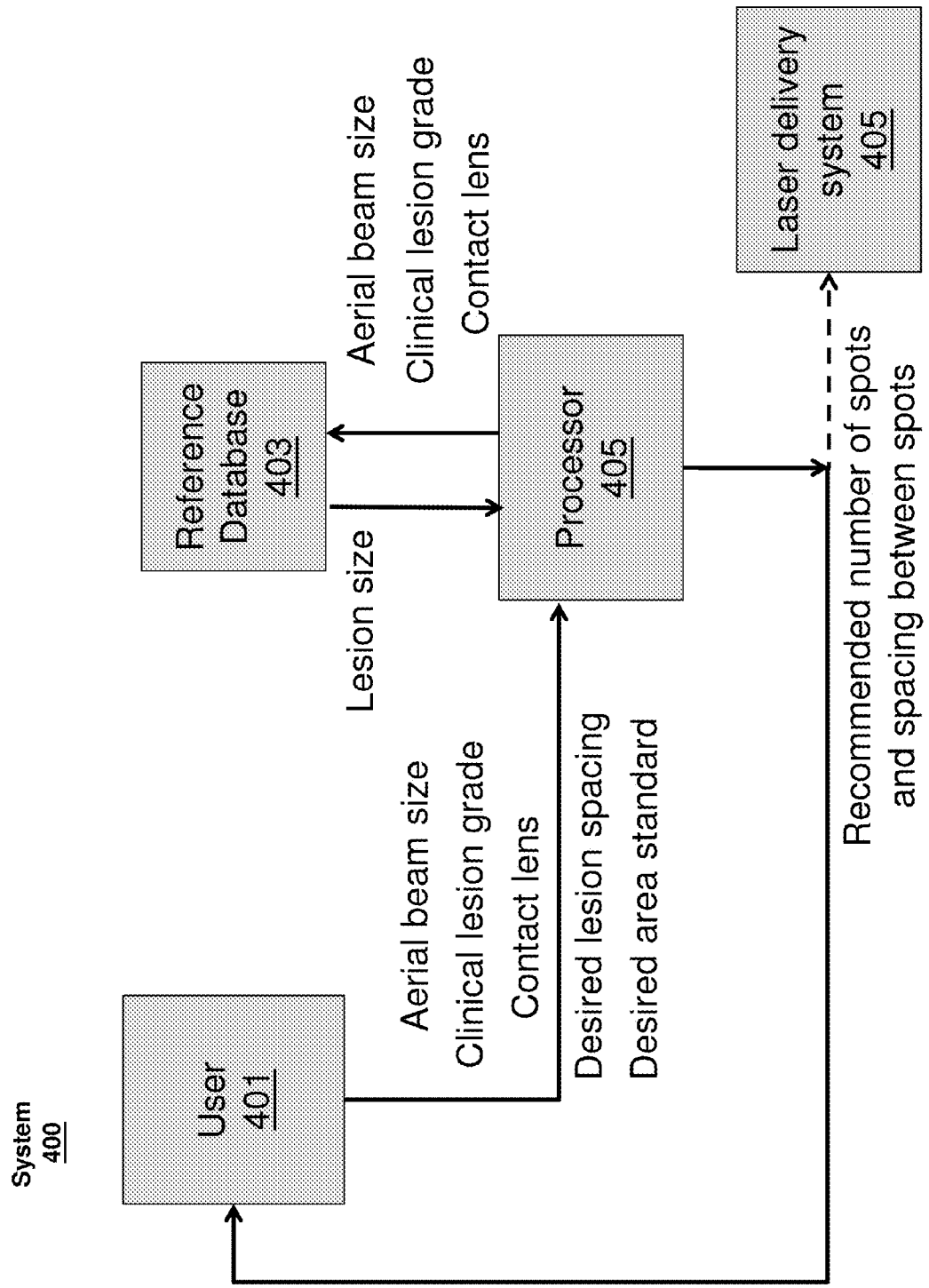
FIG. 4 illustrates exemplary laser treatment system that can be used to perform the process shown in FIG. 1.

FIG. 4 illustrates an exemplary system 400 that can be used to perform process 100. System 400 may include reference database 403 for storing reference data obtained at block 101 of process 100. System 400 may further include a general or special purpose processor 405 coupled to receive the set of laser treatment parameters (e.g., the aerial beam size, contact lens specifications, pulse duration, and clinical grade of the desired lesion) from user 401 at block 103 of process 100. Processor 405 may further receive a desired lesion pattern density (or desired spacing between the lesions) from user 401 at block 105. Processor 405 can further be coupled to query database 403 using the received laser treatment parameters (e.g., the aerial beam size, contact lens specifications, pulse duration, and clinical grade of the desired lesion) and may be coupled to receive reference data including a relationships between laser treatment parameters and resulting lesion size. Based on a direct comparison or interpolation of the received laser treatment parameters with the reference data from database 403, processor 405 may determine a recommended number of laser treatment beam spots to be applied and a spacing between the laser treatment beam spots. The determined recommended number of laser treatment beam spots and spacing between spots may be provided to user 401 (e.g., via a display included within system 400). The determined recommended number of laser treatment beam spots and spacing between spots may further be provided to laser delivery system 405 manually by user 401 or automatically from processor 405. Processor 405 may determine the recommended number of laser treatment beam spots based on predefined standards for total coagulated area (e.g., as received from user 401 or another source). For example, one standard could be defined as the equivalent coagulated area of full scatter treatment, moderate grade, 100 ms pulse duration.

While not shown, system 400 may further include a non-transitory computer-readable storage medium for providing instructions to processor 405 for execution. For example, the non-transitory computer-readable storage medium may include instructions for performing process 100, described above. Such instructions, generally referred to as "computer program code" (which may be grouped in the form of computer programs or other groupings), when executed, enable the processor to perform features or functions of embodiments of the apparatus and processes described herein. In some examples, the computer-readable storage medium may include a main memory, such as a random access memory (RAM) or other dynamic memory, for storing information and instructions to be executed by a processor. The main memory may also be used for storing temporary variables or other intermediate information during execution of instructions to be executed by the processor. The computer-readable storage medium may likewise include a read-only memory ("ROM") or other static storage device coupled for storing static information and instructions for the processor.

Figure 5:
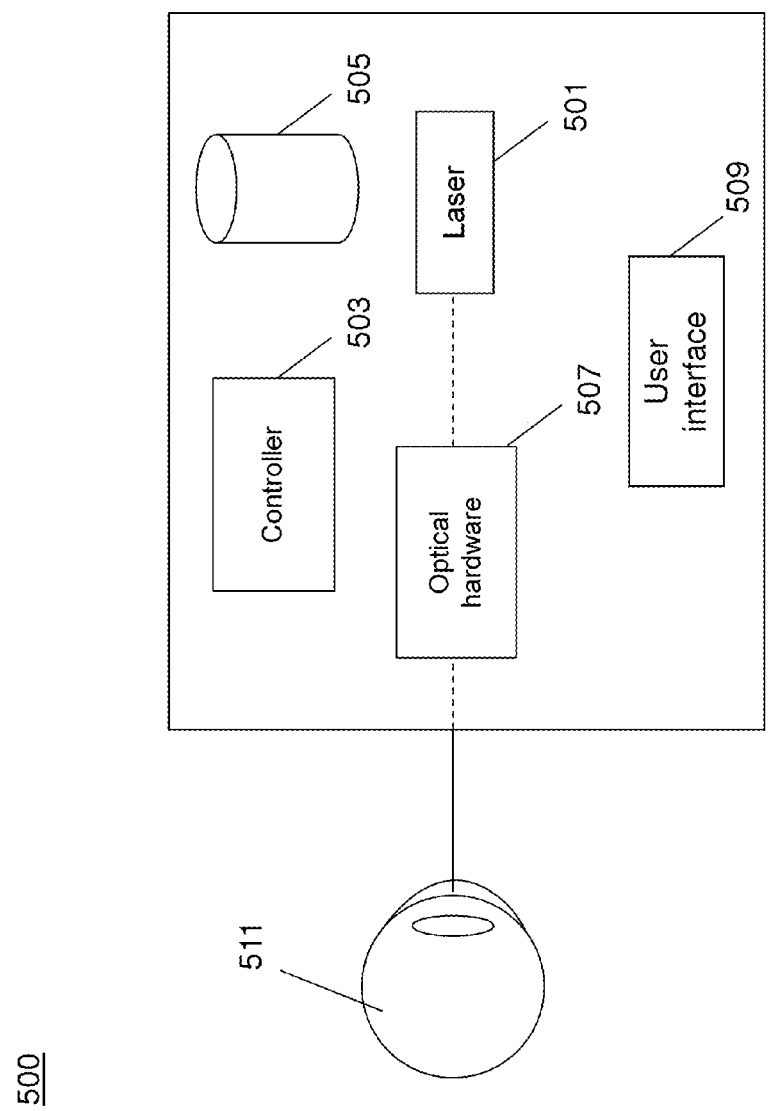
FIG. 5 illustrates an exemplary laser-treatment system for delivery of the visible or sub-visible lesions.

FIG. 5 illustrates an exemplary laser delivery system 500 that may be used as laser delivery system 405 of system 400. System 500 may include laser source 501 configured to transmit a single laser beam. In some embodiments, laser source 501 may include an Argon laser, Krypton laser, diode laser, Nd-YAG laser, or any other pulsed or continuous wave laser suitable for eye therapy. The beam generated by laser source 501 may be continuous or pulsed at a duration from about 1 ms to about 1 second, may have a power from about 30 mW to about 2 W, may have a diameter from about 50 μm to about 500 μm (e.g., about 60 μm or about 400 μm), and may have a wavelength in the visible spectrum (e.g., 532 nm, 561 nm, 577 nm, 647 nm, 659 nm, or 670 nm) or a wavelength in the non-visible spectrum (e.g., 810 nm). However, it should be appreciated that a laser source 501 producing a beam of laser energy having other characteristics may be used.

System 500 may further include optical hardware 507 for manipulating the laser beam generated by laser source 501. In some embodiments, optical hardware 507 may include a spot size selector (not shown) for adjusting the "spot size" of the laser beam delivered to the patient. The "spot size" of a beam refers to the size or diameter of the laser beam. The spot size selector may include continuous magnification change optics, a rotating turret of different magnification optics, or any other arrangement of optics used to change magnification known to those skilled in the art. The spot size selector may be configured to receive the single laser beam from laser source 501 and selectively adjust the size of the single laser beam by varying the selected magnification. The single laser beam may be aimed at the spot size selector, may be directed to spot size selector by an optical fiber, or may be directed to the spot size selector from a free-space laser source with relay or collimating optics.

In some embodiments, optical hardware 507 may further or alternatively include scanning hardware that uses the single laser beam from laser source 501 to generate a single laser beam or a patterned laser beam. In some embodiments, the scanning hardware may include a collimating lens (not shown), first and second scanning devices (not shown), such as galvanometers, MEMS devices, rotating polygons, or the like, and an optional set of relay lenses (not shown) separating the first and second scanning devices. The collimating lens may be configured to receive the laser beam. The output of the collimating lens may be a collimated beam that may be directed to a first scanning device, such as a galvanometer, MEMS device, rotating polygon, or the like. The position of the first scanning device may be precision controlled using a computerized control system (e.g., controller 503) to aim the collimated beam to a second scanning device, such as a second galvanometer, MEMS device, rotating polygon, or the like. The second scanning device may be configured to respond to the computerized control system (e.g., controller 503) to adjust the collimated beam in a direction orthogonal to the direction of adjustment of the first scanning device. In other words, the pair of scanning devices may be utilized to adjust the X-Y Cartesian position of the treatment beam. In some examples, this may be done to move a single treatment beam relative to the patient's eye 511. In other examples, the scanning devices may be synchronized with the pulses generated by the laser source 501 and cycled through several positions relatively quickly to produce a patterning effect. In the depicted system, the beam exiting the optical hardware 507 may be directed to the patient's eye 511. The treatment beam may be delivered to the patient's eye 511 using any known delivery device, such as a slit lamp, head-mounted laser indirect ophthalmoscope, handheld laser endoprobe, or the like.

System 500 may further include controller 503 for controlling laser source 501 (e.g., pulse duration, power, wavelength, etc.) and components of optical hardware 507. Controller 503 may include a general or special purpose processor configured to control the various components of system 500. Controller 503 may be coupled to receive the recommended number of laser treatment beam spots and spacing between spots from user 401 or processor 405 and control the components of system 500 accordingly. In some embodiments, system 500 may further include database 505 for storing instructions for controller 503, settings for laser source 501, and/or any other data associated with system 500.

System 500 may further include user interface 509 for allowing an operator to adjust the various settings of system 500. In some embodiments, a user interface 509 may include a knob, slider, touch screen, keyboard, display, or any other interface component, or combinations thereof, to allow the operator to interact with system 500.

While specific components are shown in FIGS. 4 and 5, it should be appreciated that systems 400 and 500 may further include other components known to those of ordinary skill in the art, such as safety devices, hardware for aiming the laser treatment beam, or the like. Moreover, while systems 400 and 500 are shown as being separate, some or all of the components of these systems can be combined into a single system. Additionally, some components may be separated or combined into a single unit. For instance, in some examples, the same general or special purpose processor can be used as processor 405 and controller 503.

It should also be appreciated that the laser spots and the corresponding lesions are not limited to round shapes, but could also be shaped otherwise. For example, the shapes can be elongated, including the line-shaped lesions with the line length much larger than its width.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the appended claims.

What is claimed is:

1. A computer-implemented method for laser treatment of an eye of a patient performed by one or more computer processors, the method comprising:
    receiving, using the one or more computer processors, a set of parameters of a laser treatment and a desired lesion pattern density, wherein the set of parameters of the laser treatment comprises one or more parameters of a laser treatment beam;
    determining, using the one or more computer processors, an estimated size of a lesion to be generated by the laser treatment beam,
        wherein the estimated size of the lesion is determined by the one or more computer processors using reference data as input,
        wherein the reference data comprises pairs of sets of parameters of laser treatments and corresponding estimated lesion sizes, and
        wherein the estimated size of the lesion is a function of the received set of parameters of the laser treatment; and
    determining, using the one or more computer processors, a recommended pattern of laser treatment beam spots that are arranged to produce a plurality of lesions in the eye of the patient that result in the desired lesion pattern density,
        wherein the recommended pattern of laser treatment beam spots is determined by the one or more computer processors using the determined estimated size of the lesion and the received desired lesion pattern density as input.

2. The method of claim 1, further comprising receiving, using the one or more computer processors, a size of a target treatment area, wherein determining the recommended pattern of laser treatment beam spots is further based on the size of the target treatment area, and wherein an application of the laser treatment beam to the eye of the patient based on the recommended pattern of laser treatment beam spots will cause a plurality of lesions to form in the eye over an area having a size corresponding to the size of the target treatment area.

3. The method of claim 1, wherein the set of parameters of the laser treatment further comprises one or more of a contact lens type, a magnification factor of a contact lens, and a desired clinical grade of the lesion.

4. The method of claim 1, wherein the set of parameters of the laser treatment further comprises a desired clinical grade of the lesion, and wherein the desired clinical grade of the lesion comprises a sub-visible lesion grade.

5. The method of claim 1, wherein determining the recommended pattern of laser treatment beam spots comprises:
    determining, using the one or more computer processors, a recommended number of laser treatment beam spots based at least in part on the determined estimated size of the lesion and the desired lesion pattern density.

6. The method of claim 1, wherein determining the recommended pattern of laser treatment beam spots comprises:
    determining, using the one or more computer processors, a recommended spacing between at least two laser treatment beam spots based at least in part on the determined estimated size of the lesion and the desired lesion pattern density.

7. The method of claim 1, wherein determining the estimated size of the lesion comprises interpolating, using the one or more computer processors, the estimated size of the lesion based on at least a portion of the reference data if values of the set of parameters of the laser treatment are excluded from the reference data.

8. The method of claim 1, further comprising applying the laser treatment beam to the eye of the patient based on the recommended pattern of laser treatment beam spots.

9. The method of claim 1, wherein the laser treatment beam comprises a patterned laser treatment beam.

10. The method of claim 1, wherein the reference data is stored in a reference database, and wherein the method further comprises:
    receiving, using the one or more computer processors, updated reference data; and
    storing, using the one or more computer processors, the updated reference data in the reference database.

11. The method of claim 1, wherein the one or more parameters of the laser treatment beam comprises one or more of an aerial beam size of the laser treatment beam and a pulse duration of the laser treatment beam.

12. The method of claim 1, further comprising:
    receiving, using the one or more computer processors, a size of a target treatment area; and wherein determining, using the one or more computer processors, the recommended pattern of laser treatment beam spots further comprises:
    determining, using the one or more computer processors, a recommended number of laser treatment beam spots and a recommended spacing between laser treatment beam spots,
        wherein the recommended number of laser treatment beam spots and the recommended spacing between laser treatment beam spots are determined by the one or more computer processors using the determined estimated size of the lesion, the received desired lesion pattern density, and the received size of the target treatment area as input.

13. A system for laser treatment of an eye of a patient, the system comprising:
    a reference database comprising reference data, wherein the reference data comprises pairs of sets of parameters of laser treatments and corresponding estimated lesion sizes;
    one or more computer processors operable to:
        receive a set of parameters of a laser treatment, wherein the set of parameters of the laser treatment comprises one or more parameters of a laser treatment beam;
        determine an estimated size of a lesion to be generated by the laser treatment beam,
            wherein the estimated size of the lesion is determined using the reference data as input,
            wherein the estimated size of the lesion is a function of the received set of parameters of the laser treatment;
        receive a desired lesion pattern density; and
        determine a recommended pattern of laser treatment beam spots that are arranged to produce a plurality of lesions in the eye of the patient that result in the desired lesion pattern density,
            wherein the recommended pattern of laser treatment beam spots is determined using the determined estimated size of the lesion and the received desired lesion pattern density as input.

14. The system of claim 13, wherein the one or more processors are further operable to receive a size of a target treatment area, wherein determining the recommended pattern of laser treatment beam spots is further based on the size of the target treatment area, and wherein an application of the laser treatment beam to the eye of the patient based on the recommended pattern of laser treatment beam spots will cause a plurality of lesions to form in the eye over an area having a size corresponding to the size of the target treatment area.

15. The system of claim 13, further comprising:
    a laser energy source configured to generate the laser treatment beam;
    a controller configured to apply the laser treatment beam based on the recommended pattern of laser treatment beam spots.

16. The system of claim 13, wherein the set of parameters of the laser treatment further comprises one or more of a contact lens type, a magnification factor of a contact lens, and a desired clinical grade of the lesion.

17. The system of claim 13, wherein the set of parameters of the laser treatment further comprises a desired clinical grade of the lesion, and wherein the desired clinical grade of the lesion comprises a sub-visible lesion grade.

18. The system of claim 13, wherein determining the recommended pattern of laser treatment beam spots comprises:
    determining a recommended number of laser treatment beam spots based at least in part on the determined estimated size of the lesion and the lesion pattern density.

19. The system of claim 13, wherein determining the recommended pattern of laser treatment beam spots comprises:
    determining a recommended spacing between at least two laser treatment beam spots based at least in part on the determined estimated size of the lesion and the lesion pattern density.

20. The system of claim 13, wherein determining the estimated size of the lesion comprises interpolating the estimated size of the lesion based on at least a portion of the reference data if values of the set of parameters of the laser treatment are excluded from the reference data.

21. The system of claim 13, wherein the laser treatment beam comprises a patterned laser treatment beam.

22. The system of claim 13, wherein the one or more processors are further operable to:
    receive updated reference data; and
    store the updated reference data in the reference database.

23. The system of claim 13, wherein the one or more parameters of the laser treatment beam comprises one or more of an aerial beam size of the laser treatment beam and a pulse duration of the laser treatment beam.

24. The system of claim 13, wherein the one or more computer processors are further operable to:
    receive a size of a target treatment area; and
    wherein determining the recommended pattern of laser treatment beam spots further comprises:
        determining a recommended number of laser treatment beam spots and a recommended spacing between laser treatment beam spots,
            wherein the recommended number of laser treatment beam spots and the recommended spacing between laser treatment beam spots are determined using the determined estimated size of the lesion, the received desired lesion pattern density, and the received size of the target treatment area as input.

25. A non-transitory computer-readable storage medium comprising computer-executable instructions executable by one or more computer processors for laser treatment of an eye of a patient, the computer-executable instructions comprising instructions for:
    receiving a set of parameters of a laser treatment and a desired lesion pattern density, wherein the set of parameters of the laser treatment comprises one or more parameters of a laser treatment beam;
    determining an estimated size of a lesion to be generated by the laser treatment beam,
        wherein the estimated size of the lesion is determined using reference data as input,
        wherein the reference data comprises pairs of sets of parameters of laser treatments and corresponding estimated lesion sizes, and
        wherein the estimated size of the lesion is a function of the received set of parameters of the laser treatment; and
    determining a recommended pattern of laser treatment beam spots that are arranged to produce a plurality of lesions in the eye of the patient that result in the desired lesion pattern density,
        wherein the recommended pattern of laser treatment beam spots is determined using the determined estimated size of the lesion and the received desired lesion pattern density as input.

26. The non-transitory computer-readable storage medium of claim 25 further comprising instructions for receiving a size of a target treatment area, wherein determining the recommended pattern of laser treatment beam spots is further based on the size of the target treatment area, and wherein an application of the laser treatment beam to the eye of the patient based on the recommended pattern of laser treatment beam spots will cause a plurality of lesions to form in the eye over an area having a size corresponding to the size of the target treatment area.

27. The non-transitory computer-readable storage medium of claim 25, wherein the set of parameters of the laser treatment further comprises one or more of a contact lens type, a magnification factor of a contact lens, and a desired clinical grade of the lesion.

28. The non-transitory computer-readable storage medium of claim 25, wherein the set of parameters of the laser treatment further comprises a desired clinical grade of the lesion, and wherein the desired clinical grade of the lesion comprises a sub-visible lesion grade.

29. The non-transitory computer-readable storage medium of claim 25, wherein determining the recommended pattern of laser treatment beam spots comprises: determining a recommended number of laser treatment beam spots based at least in part on the determined estimated size of the lesion and the desired lesion pattern density.

30. The non-transitory computer-readable storage medium of claim 25, wherein determining the recommended pattern of laser treatment beam spots comprises:
  determining a recommended spacing between at least two laser treatment beam spots based at least in part on the determined estimated size of the lesion and the desired lesion pattern density.

31. The non-transitory computer-readable storage medium of claim 25, wherein determining the estimated size of the lesion comprises interpolating the estimated size of the lesion based on at least a portion of the reference data if values of the set of parameters of the laser treatment are excluded from the reference data.

32. The non-transitory computer-readable storage medium of claim 25, wherein the laser treatment beam comprises a patterned laser treatment beam.

33. The non-transitory computer-readable storage medium of claim 25, wherein the reference data is stored in a reference database, and wherein the computer-executable instructions further comprises instructions for:
  receiving updated reference data; and
  storing the updated reference data in the reference database.

34. The non-transitory computer-readable storage medium of claim 25, wherein the one or more parameters of the laser treatment beam comprises one or more of an aerial beam size of the laser treatment beam and a pulse duration of the laser treatment beam.

35. The non-transitory computer-readable storage medium of claim 25, further comprising instructions for:
  receiving a size of a target treatment area; and
  wherein determining the recommended pattern of laser treatment beam spots further comprises:
    determining a recommended number of laser treatment beam spots and a recommended spacing between laser treatment beam spots,
    wherein the recommended number of laser treatment beam spots and the recommended spacing between laser treatment beam spots are determined using the determined estimated size of the lesion, the received desired lesion pattern density, and the received size of the target treatment area as input.

* * * * *